United States Patent
Greenberg et al.

(10) Patent No.: US 10,617,659 B2
(45) Date of Patent: *Apr. 14, 2020

(54) VALPROATE AS A TOPICAL ANTI-FUNGAL TREATMENT

(71) Applicant: Wayne State University, Detroit, MI (US)

(72) Inventors: Miriam L. Greenberg, Ann Arbor, MI (US); Rania M. Deranieh, Baltimore, MD (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/140,128

(22) Filed: Sep. 24, 2018

(65) Prior Publication Data

US 2019/0022040 A1    Jan. 24, 2019

Related U.S. Application Data

(63) Continuation of application No. 15/467,960, filed on Mar. 23, 2017, now Pat. No. 10,092,531.

(60) Provisional application No. 62/312,129, filed on Mar. 23, 2016.

(51) Int. Cl.
*A61K 31/19* (2006.01)
*A61K 9/00* (2006.01)

(52) U.S. Cl.
CPC ............ *A61K 31/19* (2013.01); *A61K 9/0014* (2013.01)

(58) Field of Classification Search
CPC ................. A61K 31/19; A61K 9/00
See application file for complete search history.

(56) References Cited

U.S. PATENT DOCUMENTS

| 4,689,334 A | 8/1987 | Kadaba | |
| 2005/0238606 A1* | 10/2005 | Dokka | A61K 8/606 424/70.13 |
| 2005/0276850 A1* | 12/2005 | Podhipleux | A61K 9/2072 424/468 |
| 2008/0107646 A1* | 5/2008 | Chung | A61K 31/19 424/131.1 |

FOREIGN PATENT DOCUMENTS

| EP | 1491188 | * 12/2004 |
| EP | 1491188 A1 | 12/2004 |
| WO | WO02069983 | 9/2002 |
| WO | WO2010093564 | 8/2010 |
| WO | WO2011097577 | 8/2011 |
| WO | WO20121287 A1 | 9/2012 |
| WO | WO2014086285 A1 | 6/2014 |

OTHER PUBLICATIONS

Lee et al (PLoS One; 7(3)e34152 (2012).*
Galcoczy et al. ActaBiolgica Hungaririca 63(4)490-500 (2012).*
"Database WPI", Week 201714, Thomson Scientific, London, GB, AN 2016-74130Y.
Deranieh, "Regulation of Inositol Biosynthesis and Cellular Consequences of Inositol Depletion: Implications for the Mechanism of Action of Valproate," Wayne State University Dissertation, 2014.
Extended European Search Report dated Jul. 5, 2017 for European Patent Application No. 17162132.9, 10 pages.
Esiobu, et al., An assessment of the in vitro antimicrobial effects of two antiepileptic drugs—sodium valproate and phenytoin, Antonie Van Leeuwenhoek, Kluwer Academic Publishers, DO, vol. 83, No. 1, Mar. 2003, pp. 63-68.
Galcoczy, et al., "In Vitro Interactions of Amantadine Hydrochloride, R-(-)-Deprenyl Hydrochloride and Valproic Acid Sodium Salt with Antifungal Agents Against Filamentous Fungal Species Causing Central Nervous System Infection," ActaBiolgica Hungaririca, vol. 63, No. 4, 2012, pp. 490-500.
Jo, et al., "Topical valproic acid increases the hair count in male patients with androgenetic alopecia: A randomized, Comparative, clinical feasibility study using phototrichogram analysis," J. Dermatol., vol. 41, No. 4, 2014, pp. 285-291.
Krajewska-Kulak and Niczyporuk, "In vitro synergistic activity of ketoconazole with valproic acid against *Candida* species," Arzneimittel-Forschung, vol. 46, No. 9, 1996, pp. 934-936.
Lee, et al, "Valproic Acid Induces Flair Regeneration in Murine Model and Activates Alkaline Phosphatase Activity in Human Dermal Papilla Cells", PLoS One, vol. 7, No. 3, 2012, pp. 1-10.
Liu, et al., "Synergistic effects of hypertonic saline and valproic acid in a lethal rat two-hit model", Journal of Trauma and Acute Care Surgery, vol. 74, No. 4, 2013, pp. 991-997.
Office Action dated Jan. 24, 2018 for U.S. Appl. No. 15/467,960, 9 pages.
Office Action dated Aug. 22, 2017 for U.S. Appl. No. 15/467,960.

* cited by examiner

*Primary Examiner* — Shirley V Gembeh
(74) *Attorney, Agent, or Firm* — Lee & Hayes, P.C.; C. Rachal Winger; Tanya M. Harding

(57) ABSTRACT

Valproate is useful as an antifungal agent. The valproate compositions can be used to treat fungal infections. The valproate compositions can be formulated as topical antifungals.

17 Claims, 4 Drawing Sheets

VALPROATE AS A TOPICAL ANTI-FUNGAL TREATMENT

CROSS-REFERENCE TO RELATED APPLICATION

This application claims priority to co-pending U.S. application Ser. No. 15/467,960 filed on Mar. 23, 2017, and claims the benefit of the earlier filing date of U.S. Provisional Application No. 62/312,129 filed on Mar. 23, 2016, both of which are incorporated herein by reference in their entirety as if fully set forth herein.

FIELD OF THE DISCLOSURE

Valproate is useful as an antifungal agent. The valproate compositions can be used to treat fungal infections. The valproate compositions can be formulated as topical antifungals and/or as salt-formulated valproate.

BACKGROUND OF THE DISCLOSURE

Fungal infections and infestations have been with us throughout the history of humanity, scientifically dating back to the frozen remains of a man living circa 3300 B.C. who had intestinal ringworm, *Trichuris trichiura*.

Throughout the last half of the 20th century, virtually all human antifungals included very strong pharmaceuticals, consequently requiring prescriptions. The majority of the prescriptions were designed to treat systemic fungal infections. Given their strength, they carried many side effects. Gradually in the 1980s and 1990s OTC antifungals emerged, and along with them came the division of the FDA currently titled the Office of Nonprescription Products.

While the last 50 years have witnessed the identification of more than 30 new pathogens, many of them fungal in origin, many areas of the world are seeing new outbreaks of known fungal infections in humans due to the increase in global business and travel coupled with rising fungal resistance.

Fungi thrive in moist dark places, whether in soil, on the surface of a plant or in vivo; most anywhere there is water or life, fungi exist. Fungi include four basic types of organisms: Yeasts; Molds; Mushrooms; and Mildew.

In humans, it has been found that fungi can infect or cause an allergic or inflammatory reaction in most any part of the body, both in the immunocompetent and in the immunocompromised, once one is sensitized. The most commonly reported fungal infections are candidiasis, both *Candida albicans* and *C. non-albicans* varieties, and *Aspergillus*. There are 500 fungi known to infect humans, and a few of them are lethal. 40% of all deaths from nosocomial infections in the last 20 years have been caused by a fungal pathogen. Science is showing that both the number of systemic infections and drug resistance is on the rise. Once a person is sensitized to a fungus their immunity to fungal pathogens decreases over time and recurrence is often more common.

There are more than 110 therapies that have been tested in humans; a good number of them are currently less effective than when originally approved. Presently there are numerous new therapies in development; nonetheless, it should be noted that in the case of invasive or systemic disease such as aspergillosis, monotherapy has less than a 50% success rate.

Fungal spores are linked to allergic sinusitis, hypersensitivity pneumonitis and atopic dermatitis, and are often considered to be a major cofactor in these multi-factorial conditions. More than 30 million people in the U.S. have been diagnosed with asthma, and they are often sensitized to one or another variety of fungi.

Research shows that many human populations are now at risk for fungal infections that previously only occurred within more isolated populations of the world. If one couples this fact with the increase in organ transplants and comorbid disease states such as HIV/AIDS, diabetes, cancer or other diseases that compromise the immune system, which very often put individuals at higher risk of developing a life-threatening or potentially life-threatening fungal infection, there is no doubt that fungal infections are on the rise. As an example of those with comorbid illness, in 2008 more than 12.7 million people were diagnosed with cancer and some 7.6 million died of cancer, many of which during the course of their treatment had either a compromised immune system, hospitalization or an implantable device that left them susceptible to infection, whether of fungal origin or some other pathogen.

SUMMARY OF THE DISCLOSURE

The present disclosure provides valproate compositions as anti-fungal treatments. The compositions can be topical and/or salt-formulated.

BRIEF DESCRIPTION OF THE FIGURES

FIG. 3A. For each sample, 300-500 cells were counted and the percentage of cells forming hyphal structures was calculated. Values represent the mean of three independent experiments±S.E. (error bars). FIG. 3B, Phase contrast images of representative cells observed at magnification 1000×.

FIG. 4A. For each sample, 300-500 cells were counted and the percentage of cells forming hyphal structures was calculated. Values represent the mean of three independent experiments±S.E. (error bars). FIG. 4B, Phase contrast images of representative cells observed at magnification 1000×.

DETAILED DESCRIPTION

Figure 1:
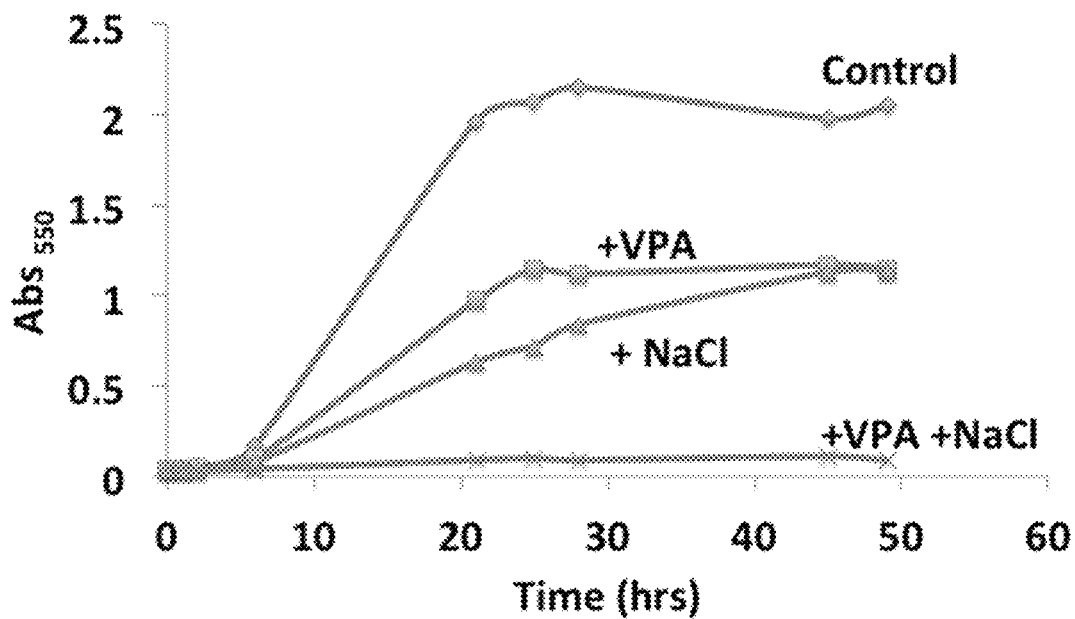
FIG. 1. The combined effect of osmotic stress and valproate (VPA) is deleterious to yeast cells.

A fungal infection includes the excessive growth of fungi that are normally present in or on the body of a subject or the growth of fungi that are not normally present in or on a subject. Fungal infections are known as mycoses and are classified into four groups based on the level of penetration into the body tissues. Superficial mycoses are caused by fungi that grow on the outermost layer of the skin and hair and cause little or no inflammatory response. Cutaneous mycoses extend into the epidermis and include invasive hair and nail diseases. Subcutaneous mycoses penetrate into the dermis, subcutaneous tissues, muscle, and fascia. Systemic mycoses infect the internal organs and disseminate throughout the body.

An example of superficial mycoses is *Tinea versicolor*. With *Tinea versicolor*, the fungus interferes with the pigmentation of the skin and the affected areas appear as discolored patches of skin. *Tinea versicolor* occurs most frequently in teens and young adults.

Examples of cutaneous mycoses include common athlete's foot and ringworm. Some common symptoms for these infections include itching and/or burning of the skin; redness and blisters on the skin; and peeling, cracking, and scaling of the skin. Other examples include onychomycosis, which is fungal infection of the nail.

Examples of cutaneous mycoses also include mucocutaneous mycoses such as oral thrush, vaginal thrush, and penile thrush. Symptoms for oral thrush include white patches on the tongue or other areas of the mouth and throat and may also include soreness and problems with swallowing. Symptoms of vaginal thrush include genital itching, burning, and white discharge from the vagina. Penile thrush is less common, and itchiness is the symptom of penile thrush.

Subcutaneous mycoses is caused by traumatic inoculation of the fungi into the subcutaneous tissue. These infections are difficult to treat and may require surgical removal. Examples of subcutaneous mycoses include chromoblastomycosis, mycetoma, and sporotrichosis. Chromoblastomycosis is characterized by verrucoid lesions of the skin of the lower extremities. It starts out as a small red or grey bump and grows slowly into a warty dry nodule or plaque. New lesions may develop as satellites. Chromoblastomycosis is limited to the subcutaneous tissue, with no involvement of bone, tendon, or muscle. In contrast, mycetoma involves the contiguous bone, tendon, and skeletal muscle. Mycetoma is characterized by the formation of grains containing aggregates of the fungi that may be discharged onto the skin surface through multiple sinuses. Sporotrichosis is the infection of the skin caused by a fungus related to the mold of stale bread. The first symptom is a firm but painless bump on the skin that can range in color from pink to purple. Over time, the bump may develop into an open sore that may drain clear fluid. Untreated the sore becomes chronic. In most cases, the mold spreads along the lymph nodes and new nodules and sores spread up in a line up the infected arm or leg.

Systemic mycoses can be caused by primary pathogens or opportunistic pathogens. Systemic mycoses caused by primary pathogens usually originate in the lungs and spread to many organ systems. Examples of systemic mycoses caused by primary pathogen include histoplasmosis and blastomycosis. Histoplasmosis is a pulmonary infection resulting from inhalation of the fungus *Histoplasma capsulatum*. It can be fatal if left untreated. Blastomycosis is a primary pulmonary infection resulting from inhalation of *Blasotmyces dermatitidis*. It can disseminate to the skin, bone, and the prostate.

Systemic mycoses caused by opportunistic pathogens are infections of patients with immune deficiencies, for example, patients with AIDS and metastatic cancer. Examples of opportunistic mycoses include Candidiasis, Cryptococcosis, and Aspergillosis.

Candidiasis can be classified as superficial or deep. Superficial candidiasis may involve the mucosal surfaces including the oral cavity, the pharynx, the esophagus, and the vagina. Deep candidiasis involves organs such as kidneys, liver, spleen, brain, eyes, and heart.

Cryptococcosis most frequently causes pneumonia and/or meningitis. Weakened immune system is the common risk factor for developing cryptococcosis.

Aspergillosis is caused by breathing *Aspergillus* spores which is a common mold. Most people breathe the spores without getting sick. However, people with a weakened immune system or lung disease are at a higher risk of developing health problems due to *Aspergillus*. The fungus may disseminate from the lungs to the brain, kidneys, liver, heart, and bones.

In general, systemic fungal infections are chronic. They may develop slowly, and may take weeks or months to become a problem. Symptoms are sometimes similar to those of the common cold, but in people with weakened immune systems, symptoms may be sudden and severe, requiring hospitalization. Symptoms may include cough, fever, chills, night sweats, loss of appetite, weight loss, general fatigue, and depression.

Particular embodiments disclosed herein show that VPA, in *Saccharomyces cerevisiae*, perturbs the biosynthesis of fungus cell wall components. Further, a mixture at a low salt concentration inhibited the growth of yeast cells. VPA was further tested on *C. albicans*, which relies on its hyphae for its virulence and tissue penetration. In the presence of VPA, transformation of *Candida* yeast cells into hyphae forming cells was greatly reduced. VPA may compromise the virulence of opportunistic fungi by perturbing the formation of hyphae required for virulence and infectivity.

Fungal infections can be caused by *Aspergillus, Blastomyces, Candida, Coccidioides Cryptococcus, Histoplasma, Pneumocystis, Coccidioides, Stachybotrys, Microsporum, Epidermophyton*, or *Trichophyton*.

Many anti-fungal drugs available on the market target eukaryotic components that are common to both fungi and humans. VPA is an ideal candidate as a novel antifungal agent because it inhibits the synthesis of a structure that has no counterpart in humans.

Valproic acid (di-n-propyl acetic acid), the acid form of VPA, is widely used in neurological and psychiatric disorders. Valproic acid dissociates to the VPA ion in the gastrointestinal tract. Valproic acid and sodium VPA have been approved for the treatment of epilepsy, bipolar disorder, and migraine. They can be administered orally or intravenously. Valproic acid has the following structural formula:

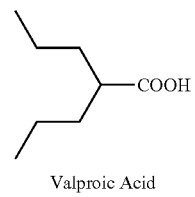

Valproic Acid

Formula (I) Valproic Acid has a simple short structure of a short branched fatty acid chain.

Over the years, many analogs of VPA have been synthesized in the process of developing antiepileptic drugs with improved tolerability and efficacy. Examples of such analogs include the amide derivatives such as propyl isopropyl acetamide (PID), valrocemide (valpropyl glycinamide), 2-ethyl-3-methylpentamide (valnoctamide), diisopropylacetamide, 2-propylpentanamide, N,N-di propyl-2-propylpentamide; the cyclic derivatives such as N-methyl-2,2,3,3-tetramethylcyclopropylamide (MTMCD), N-methoxy-2,2,3,3-tetramethylcyclopropanecarboxamide (N-methoxy- TMCD), Tetramethyl-cyclopropanecarbonylurea (TMCU); the ester derivatives such as 1-O-(2-propylpentanoyl)-2,3-propandiol, 2,2-di(hydroxymethyl)-1-O-(2-propylpentanoyl)-1,3-propanediol and 2,2-di(hydroxymethyl)-1,3-di-O-(2-propylpentanoyl)-1,3-propanediol; the structural analogs 1-cycloheptene-1-carboxylic acid and cyclooctanecarboxylic acid; the small VPA-ester, 2-propylpentanoic acid ethyl ester; and the mannitol-esters 1-O-(2-propylpentanoyl)-D-mannitol and 3,4;5,6-Di-O-isopropylidene-1-O-(2-propylpentanoyl)-D-mannitol.

The term Valproate refers to VPA or a salt, solvate, hydrate, analog, or derivative of VPA and includes a salt, solvate, hydrate, active metabolite, prodrug, stereoisomer (including enantiomers and diastereomers) of an analog or derivative of VPA.

The term "analog" (also "structural analog" or "chemical analog") is used to refer to a compound that is structurally similar to another compound but differs in one or more atoms, functional group, or substructure. Analogs can have very different physical, chemical, biochemical, or pharmacological properties. A derivative in chemistry is a compound that is obtained from a similar compound or a precursor compound by a chemical reaction.

Exemplary VPA analogs include:

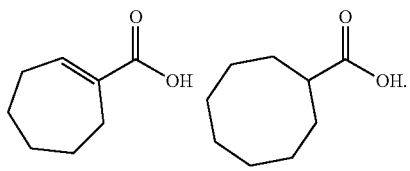

1-cycloheptene-1-carboxylic acid, and cyclooctanecarboxylic acid

Exemplary amide derivatives of VPA include:

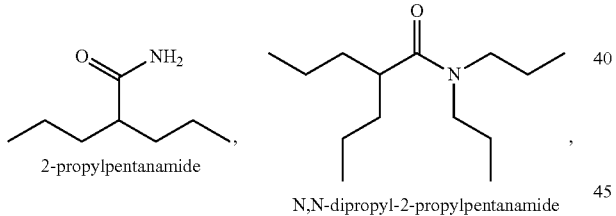

2-propylpentanamide

N,N-dipropyl-2-propylpentanamide

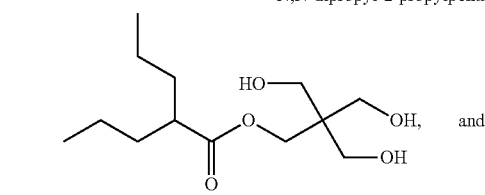

2,2-di(hydroxymethyl)-1-O-(2-propylpentanoyl)-1,3-propanediol

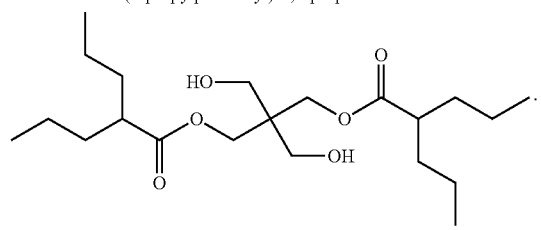

2,2-di(hydroxymethyl)-1,3-di-O-(2-propylpentanoyl)-1,3-propanediol

Additional examples include:

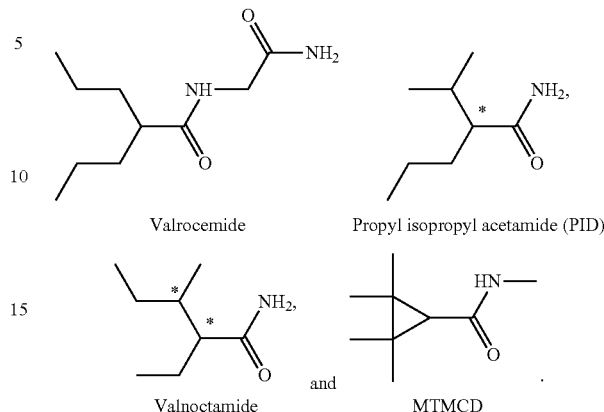

Valrocemide

Propyl isopropyl acetamide (PID)

Valnoctamide and

MTMCD

Mannitol-ester derivatives of VPA include:

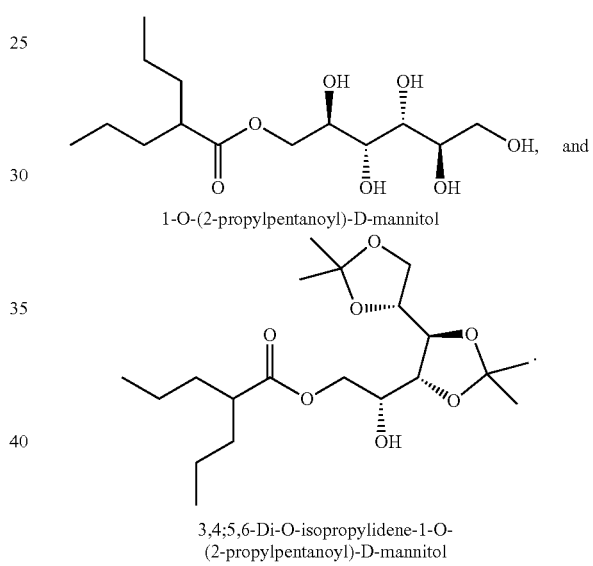

1-O-(2-propylpentanoyl)-D-mannitol 3,4;5,6-Di-O-isopropylidene-1-O-(2-propylpentanoyl)-D-mannitol An ester derivative of VPA includes:

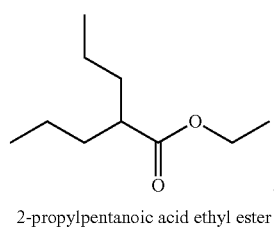

2-propylpentanoic acid ethyl ester

Salts of VPA include those prepared with an organic acid or an inorganic acid. Examples of organic acids include acetic acid, trifluoroacetic acid, trichloroacetic acid, propionic acid, glycolic acid, pyruvic acid, succinic acid, benzoic acid, cinnamic acid, mandelic acid, methanesulphonic acid, para-toluenesulphonic acid, salicylic acid, picric acid, citric acid, oxalic acid, tartaric acid, malonic acid, maleic acid, camphor-sulphonic acid and fumaric acid. Examples of inorganic acids include hydrohalic acids such as hydrochloric acid and hydrobromic acid, sulphuric acid, nitric acid and phosphoric acid.

Salts of VPA also include those prepared with an organic base or an inorganic base. Examples of organic bases include amines such as aliphatic or aromatic primary, secondary or tertiary amines such as methylamine, ethylamine, ethanolamine, propylamine, isopropylamine, the four isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline and isoquinoline. Examples of inorganic bases include hydroxides of alkali metals or of alkaline-earth metals or carbonates of alkali metals or of alkaline-earth metals. Specific examples of these bases include potassium hydroxide, sodium hydroxide, lithium hydroxide, calcium hydroxide, potassium carbonate, sodium carbonate and calcium carbonate.

In particular embodiments, the compositions disclosed herein includes VAL or valproic acid and a salt. Examples of salts include sodium chloride, potassium chloride, calcium chloride, sodium hydrogen phosphate, or potassium hydrogen phosphate.

In particular embodiments, the compositions disclosed herein can be formulated for topical administration. The compositions disclosed herein can also be formulated for intradermal, intralesional, intraocular, intravaginal, intramuscular, and/or subcutaneous administration.

In particular embodiments, or topical administration, the formulation can further include a penetration enhancer. The penetration enhancer can be a skin penetration enhancer. A skin penetration enhancer is a molecule that promotes the diffusion of VAL through the skin. A variety of compounds have been shown to be effective skin penetration enhancers. See, Percutaneous Penetration Enhancers (Smith et al., CRC Press, Inc., Boca Raton, Fla. 1995). Exemplary skin penetration enhancers include sulfoxides such as dimethylsulfoxide (DMSO) and decylmethylsulfoxide (CioMSO); ethers such as diethylene glycol monoethyl ether and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin; the 1-substituted azacycloheptan-2-ones, particularly I-n-dodecylcyclazacycloheptan-2-one; alcohols such as ethanol, propanol, octanol, benzyl alcohol, etc.; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate; amides and other nitrogenous compounds such as urea, dimethylacetamide (DMA), dimethylformamide (DMF), 2-pyrrolidone, l-methyl-2-pyrrolidone, ethanolamine, diethanolamine and triethanolamine; terpenes; alkanones; organic acids, particularly salicylic acid and salicylates, citric acid, and succinic acid; polyacrylic acids such as a carbomer (CARBOPOL™, B. F. Goodrich Company) and copolymers of C10 to C30 alkyl acrylates and one or more monomers of acrylic acid, methacrylic acid or one of their simple esters crosslinked with an allyl ether of sucrose or an allyl ether of pentaerythritol (PERMULEN™, B.F. Goodrich Company); galactomannan gums such as guar gum or locust bean gum; polysaccharide gum such as agar gum, alginate, carob gum, carrageen gum, ghatti gum, guar gum, karaya gum, kadaya gum, locust bean gum, rhamsan gum, xanthan gum, or a mixture thereof; and cellulose derivatives such as ethyl cellulose, methyl cellulose, hyrdoxypropyl cellulose, and mixtures thereof.

In particular embodiments, the compositions can be in the form of, e.g., gels, ointments, pastes, lotions, creams, sprays, foams, or powders.

A gel is a substantially dilute cross-linked system, which exhibits no flow when in the steady-state. Most gels are liquid, however they behave more like solids due to the three-dimensional cross-linked network within the liquid. Gels can have properties ranging from soft and weak to hard and tough.

An ointment is a homogeneous, viscous, semi-solid preparation, most commonly a greasy, thick oil (oil 80%-water 20%) with a high viscosity. Ointments have a water number, which is the maximum quantity of water that 100 g of a base can contain at 20° C.

A paste includes three agents—oil, water, and powder, one of which includes a therapeutic agent. Pastes can be an ointment in which a powder is suspended.

A lotion also includes oil, water, and powder, but can have additional components (e.g., alcohol to hold the emulsion together) and often has a lower viscosity than a paste.

A cream is an emulsion of oil and water in approximately equal proportions. Creams are thicker than lotions and maintain their shape when removed from a container.

Topical formulations disclosed herein can include components, such as animal and vegetable fats, oils, waxes, paraffins, starch, tragacanth, cellulose derivatives, polyethylene glycols, silicones, bentonites, silicic acid, talc and zinc oxide, or mixtures thereof. In particular embodiments, topical formulations may include thickening agents, surfactants, organic solvents, and/or tonicity modifiers.

In particular embodiments, topical formulations can be prepared using thickening agents, such as carboxymethylcellulose sodium, sodium starch glycollate type C, or Carbomers such as CARBOPOL® (Lubrizol Advanced Materials, Inc. Cleveland, Ohio, USA) 934, 980, 981, 1382, 5984, or 2984. In particular embodiments, topical formulations can be prepared using surfactants, such as PLURONIC® (BASF Corporation, Mount Olive, N.J., USA) co-polymers, such as Pluronic® F-127, and/or a PLURONIC® co-polymer having the formula

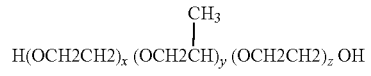

or H[OCH2CH2]49[OCHCH2]67[OCH2CH2]49OH; propyl glycol, polypropylene glycol (PPG) stearyl ethers, such as PPG ethers of stearyl alcohol including PPG-20 methyl glucose ether distearate, PPG-15 Stearyl Ether, and PPG-11 Stearyl Ether.

In particular embodiments, topical formulations such as gel formulations may include an organic solvent (e.g. a lower alkyl alcohol, such as ethyl alcohol or isopropyl alcohol; a ketone, such as acetone or N-methyl pyrrolidone; a glycol, such as propylene glycol; and the like, or mixtures thereof) present in an amount of 1% to 99%. In particular embodiments, an organic solvent may be present in an amount of 60% to 80%. In particular embodiments, topical formulations may include a cellulose derivative, such as hydroxyl ethyl cellulose, hydroxy propyl cellulose, hydroxy propyl methyl cellulose, methyl cellulose, carboxy methyl cellulose, sodium carboxy methyl cellulose, ethyl cellulose, and the like, or combinations thereof present in an amount of 0.1% to 20%. In particular embodiments a cellulose derivative may be present in an amount of 0.5% to 5%.

In particular embodiments, topical formulations such as gel formulations include any suitable tonicity modifier. Exemplary suitable tonicity modifiers include sodium chloride, potassium chloride, mannitol, sucrose, lactose, fructose, maltose, dextrose, dextrose anhydrous, propylene glycol, and glycerol. In particular embodiments, the tonicity modifier can be present in an amount of 0.5% to 1% by weight. In particular embodiments, a tonicity modifier can be present in an amount of 0.8% to 1% by weight of the topical formulation. In particular embodiments, buffers can be present in the topical formulations. Exemplary buffers include phosphate buffered saline (PBS) acetate buffers, such as sodium acetate trihydrate or glacial acetic acid; and citrate buffers, such as sodium citrate dihydrate and citric acid.

In particular embodiments, topical formulations such as gel formulations may have a viscosity of at least 1,000 centipoise (cps). In particular embodiments, topical formulations such as gel formulations may have a viscosity of at least 3,000 cps. In particular embodiments, the viscosity of topical formulations will not exceed 50,000 cps.

Powders and sprays particularly may benefit from the inclusion of excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. The compositions of the disclosure can be alternatively administered by aerosol. This is accomplished by preparing an aqueous aerosol, liposomal preparation, or solid particles containing a composition of the disclosure. A non-aqueous (e.g., fluorocarbon propellant) suspension also could be used. Sonic nebulizers can be preferred because they minimize exposing the compositions to shear, which can result in degradation of the composition.

Compositions can also be incorporated into wound dressings (e.g., bandages, adhesive bandages, transdermal patches). Generally, in these embodiments, compositions are embedded within puffs, gauzes, fleeces, gels, powders, sponges, or other materials that are associated with a second layer to form a wound dressing. Absorption enhancers can also be used to increase the flux of the composition, and particularly the therapeutic protein within the composition, across the skin. The rate of such flux can be controlled by either providing a rate controlling membrane or dispersing the therapeutic protein in a polymer matrix or gel.

In particular embodiments, the second layer of a wound dressing can be an elastomeric layer, vapor-permeable film, waterproof film, a woven or nonwoven fabric, mesh, or the like. The composition containing layer and second layer can be bonded using any suitable method (e.g., the application of adhesives, such as pressure sensitive adhesives, hot melt adhesives, curable adhesives; the application of heat or pressure, such as in lamination; a physical attachment through the use of stitching, studs, other fasteners; or the like).

Wound dressings may include adhesives for attachment to the skin or other tissue. Although any adhesive suitable for forming a bond with the skin or other tissue can be used, in particular embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability of a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

In particular embodiments, the pressure sensitive adhesive can include a butyl acrylate. While butyl acrylate pressure sensitive adhesives can generally be used for many applications, any pressure sensitive adhesive suitable for bonding skin can be used. Such pressure sensitive adhesives are well known in the art.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with therapeutic compositions disclosed herein. Treating subjects includes delivering therapeutically effective amounts. Therapeutically effective amounts include those that provide effective amounts, prophylactic treatments, and/or therapeutic treatments.

An "effective amount" is the amount of a composition necessary to result in a desired physiological change in the subject. Effective amounts are often administered for research purposes. Effective amounts disclosed herein treat a fungal infection.

A "prophylactic treatment" includes a treatment administered to a subject who is at risk for or displays early signs or symptoms of a fungal infection such that treatment is administered for the purpose of diminishing, preventing, or decreasing the risk of the fungal infection worsening or becoming chronic. Thus, a prophylactic treatment functions as a preventative treatment against development or further development of fungal infections.

A "therapeutic treatment" includes a treatment administered to a subject who has a fungal infection and is administered to the subject for the purpose of treating the existing fungal infection.

Objective measures for treating fungal infections can be those used by clinicians in the field. Such measures may include a decrease in the surface area of an affected area, a measurable reduction in redness, swelling, scaling, etc. Subjective subject feedback can also be used. Subjective feedback can include a reduction in, for example, itchiness or burning.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by a physician, veterinarian, or researcher taking into account parameters such as physical and physiological factors including target, severity of infection, type of infection, and previous or concurrent therapeutic interventions.

Useful doses can often range from 0.1 to 5 µg or from 0.5 to 1 µg. In other examples, a dose can include 1 µg, 5 µg, 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 150 µg, 200 µg, 250 µg, 350 µg, 400 µg, 450 µg, 500 µg, 550 µg, 600 µg, 650 µg, 700 µg, 750 µg, 800 µg, 850 µg, 900 µg, 950 µg, 1000 µg, 0.1 to 5 mg or from 0.5 to 1 mg. In other examples, a dose can include 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 350 mg, 400 mg, 450 mg, 500 mg, 550 mg, 600 mg, 650 mg, 700 mg, 750 mg, 800 mg, 850 mg, 900 mg, 950 mg, 1000 mg, or more.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly.

Further helpful definitions supporting this disclosure include: *Candida Albicans* (*C. albicans*): A diploid fungus that grows both as yeast and filamentous cells and a causal agent of opportunistic oral and genital infections in humans and candidal onychomycosis, an infection of the nail plate. *C. albicans* is commensal and a constituent of the normal gut flora comprising microorganisms that live in the human mouth and gastrointestinal tract. Overgrowth of the fungus results in candidiasis (candidosis). Candidiasis is often observed in immunocompromised individuals, including HIV-infected patients. A common form of candidiasis restricted to the mucosal membranes in mouth or vagina is thrush, which is usually easily cured in people who are not immunocompromised. To infect host tissue, the usual unicellular yeast-like form of *C. albicans* reacts to environmental cues and switches into an invasive, multicellular filamentous form, a phenomenon called dimorphism.

Endocytosis: a form of active transport in which a cell transports molecules (such as proteins) into the cell by engulfing them in an energy-using process.

Figure 6:
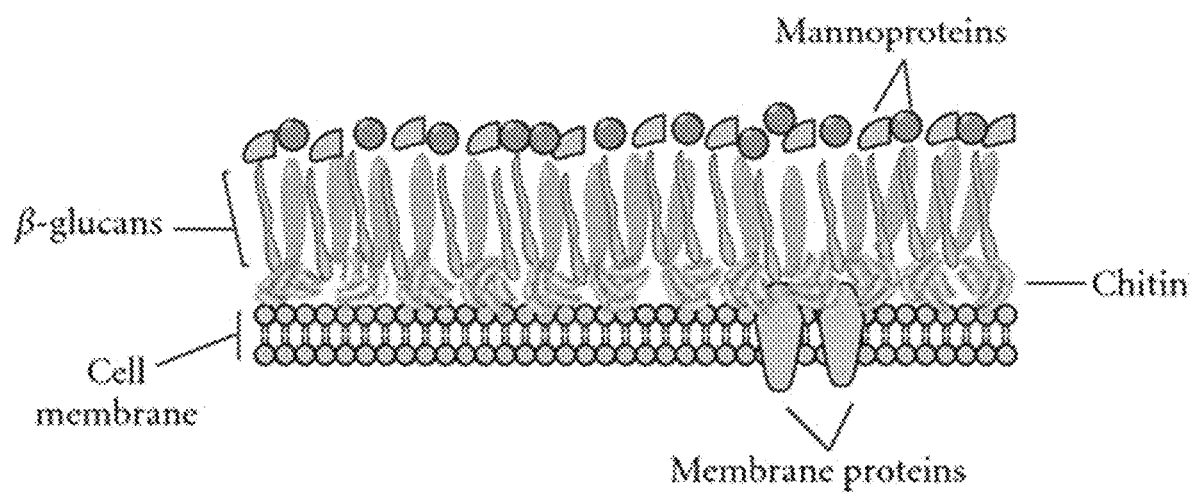
FIG. 6. Most structural proteins present in cell wall are glycosylated and contain mannose. They are mannoproteins or mannans.

Fungal Cell Wall: In fungi, the cell wall is the outer-most layer, external to the plasma membrane. The fungal cell wall is a matrix of three main components:
1. Chitin: polymers consisting mainly of unbranched chains of β-(1,4)-linked-N-Acetylglucosamine in the Ascomycota and Basidiomycota, or poly-β-(1,4)-linked-N-Acetylglucosamine (chitosan) in the Zygomycota. Both chitin and chitosan are synthesized and extruded at the plasma membrane.
2. Glucans: glucose polymers that function to cross-link chitin or chitosan polymers. β-glucans are glucose molecules linked via β-(1,3)- or β-(1,6)-bonds and provide rigidity to the cell wall while α-glucans are defined by α-(1,3)- and/or α-(1,4) bonds and function as part of the matrix.
3. Proteins: enzymes necessary for cell wall synthesis and lysis in addition to structural proteins are all present in the cell wall. Most of the structural proteins found in the cell wall are glycosylated and contain mannose, thus these proteins are called mannoproteins or mannans (see FIG. 6).

Hyphae: a long, branching filamentous structure of a fungus, oomycete, or actinobacterium. In most fungi, hyphae are the main mode of vegetative growth, and are collectively called a mycelium. Yeasts are unicellular fungi that do not grow as hyphae.

Yeast: eukaryotic microorganisms classified as members of the fungus kingdom with 1,500 species currently identified and are estimated to constitute 1% of all described fungal species.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A topical formulation including a therapeutically effective amount of valproate (VPA) or valproic acid; and a salt.
2. The topical formulation of embodiment 1, wherein the formulation further includes a penetration enhancer.
3. The topical formulation of embodiment 1 or 2, wherein the penetration enhancer is a sulphoxide, an ether, a surfactant, an alcohol, a polyol, a fatty acid, an amide, a pyrrolidone, a terpene, or an azone.
4. The topical formulation of any one of embodiments 1-3, wherein the VPA is sodium VPA.
5. The topical formulation of any one of embodiments 1-4, wherein the salt is sodium chloride, potassium chloride, calcium chloride, sodium hydrogen phosphate, or potassium hydrogen phosphate.
6. The topical formulation of any one of embodiments 1-5, wherein the salt is sodium chloride.
7. A method of treating a fungal infection in a subject, wherein the method includes administering the topical formulation of any one of embodiments 1-6 to the subject, thereby treating a fungal infection.
8. The method of embodiment 7, wherein the fungal infection is athlete's foot, penile thrush, ringworm, oncomycosis, thrush, vaginal yeast infection, or fungal eye infection.
9. The method of embodiment 7 or 8, wherein the fungal infection is caused by *Candida, Histoplasma, Microsporum, Epidermophyton, Trichophyton*, or a combination thereof.
10. A method of treating a fungal infection in a subject, wherein the method includes administering a formulation including VPA or valproic acid and a salt.
11. The method of embodiment 10, wherein the fungal infection includes systemic mycoses.
12. The method of embodiment 10 or 11, wherein the fungal infection is caused by *Aspergillus, Blastomyces, Candida, Cryptococcus, Histoplasma, Pneumocystis, Coccidioides, Stachybotrys, Microsporum, Epidermophyton, Trichophyton*, or a combination thereof.
13. The method of any one of embodiments 10, 11, or 12, wherein the salt is sodium chloride, potassium chloride, calcium chloride, sodium hydrogen phosphate, or potassium hydrogen phosphate.
14. The method of any one embodiments 10-13, wherein the salt is sodium chloride.

Example 1

The combined effect of osmotic stress and valproate (VPA) is deleterious to yeast cells. Wild type *Saccharomyces cerevisiae* cells (strain BY4741) were grown in synthetic medium in the presence or absence of VPA and/or NaCl. Cells were incubated at 30° C., and growth was monitored spectrophotometrically by measuring absorbance at 550 nm. Growth was decreased by 50% when cells were grown in the presence of either VPA or NaCl, however when used in combination, VPA and NaCl had a detrimental effect on growth of yeast cells. See FIG.

Example 2

Figure 2:
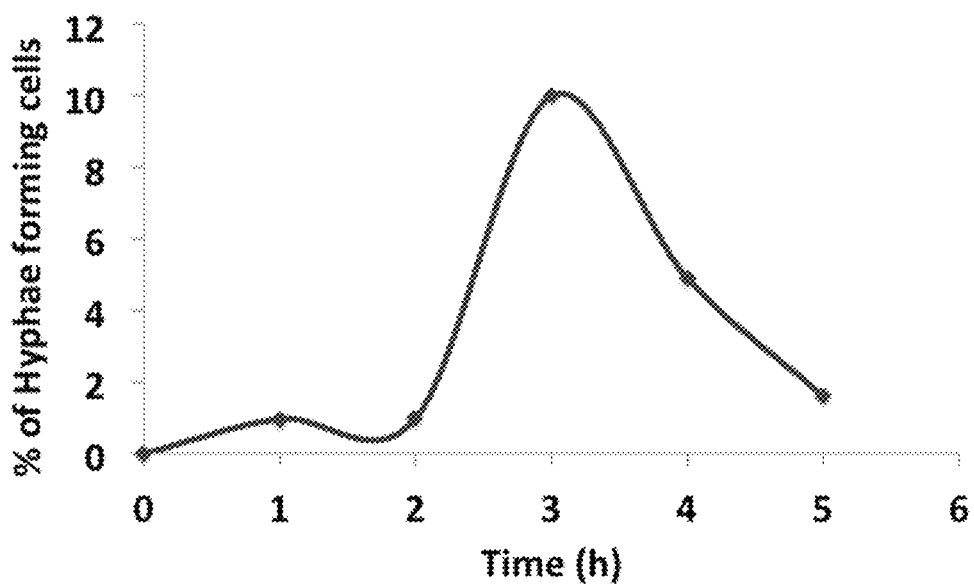
FIG. 2. Hyphae formation is at its peak after 3 hours of incubation at 37° C. at 200 rpm.

Hyphae formation is at its peak after 3 hours of incubation at 37° C. at 200 rpm. An overnight culture of *Candida albicans* (Strain Sc 5314) was prepared using serum-free RPMI-64 medium. Cells were pelleted at 7,500×g and resuspended in RPMI-64 supplemented with 10% Fetal Bovine Serum (FBS) to induce hyphae formation. Cultures were incubated at 37° C. in a rotary shaker at 200 rpm. Samples were drawn out at one-hour intervals and observed for development of hyphal structures. See FIG. 2

Example 3

Figure 3A:
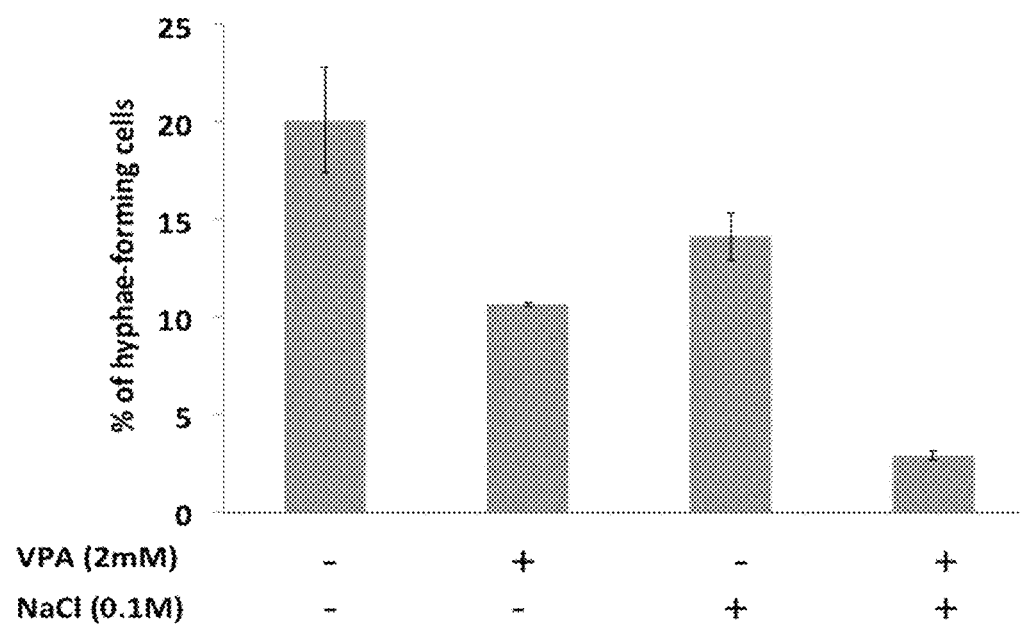
FIGS. 3A and 3B. Valproate (VPA) combined with NaCl greatly decreases the formation of hyphae in *Candida* cells.
Figure 3B:
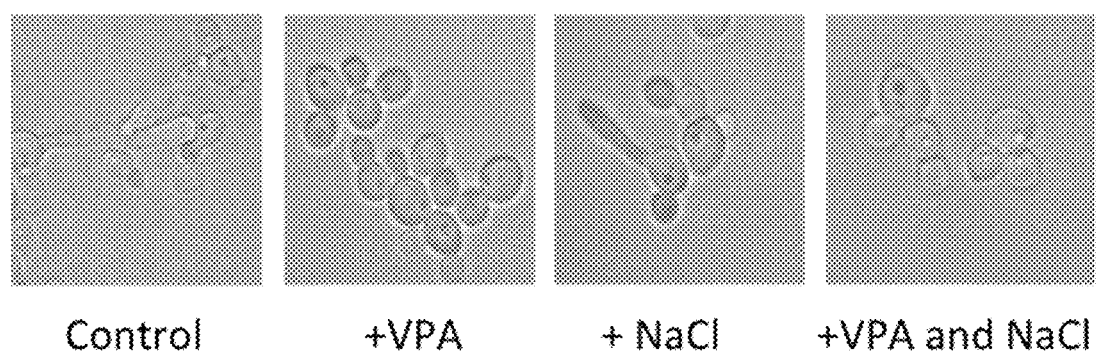

Valproate (VPA) combined with NaCl greatly decreases the formation of hyphae in *Candida* cells. An overnight culture of *C. albicans* was prepared using serum-free RPMI-64 medium. Cells were pelleted at 7,500×g and resuspended in RPMI-64/10% FBS with or without 0.1M NaCl and/or 2 mM VPA as indicated. Cultures were incubated at 37° C. in a rotary shaker at 200 rpm for 3 hours. For each sample, 300-500 cells were counted and the percentage of cells forming hyphal structures was calculated. Values represent the mean of three independent experiments±S.E. (error bars). See FIG. 3A. Phase contrast images of representative cells observed at magnification 1000× are shown in FIG. 3B.

Example 4

Figure 4A:
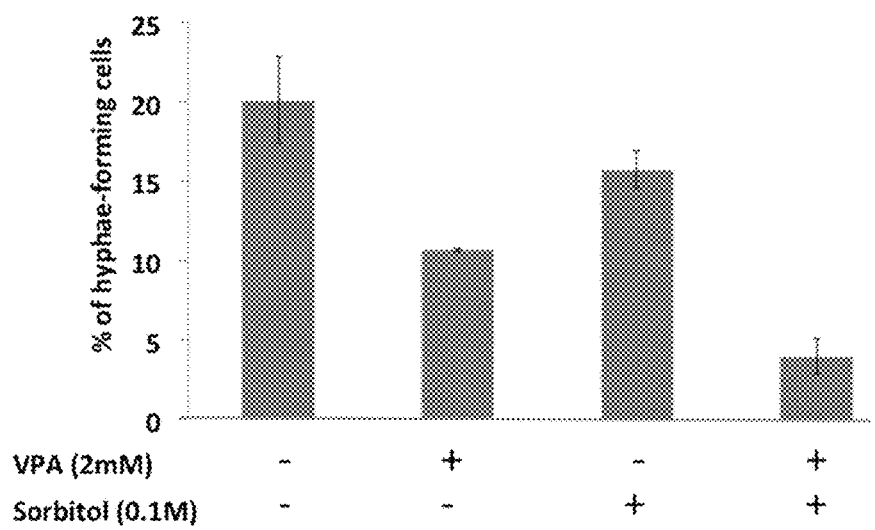
FIGS. 4A and 4B. Valproate combined with Sorbitol greatly decreases the formation of hyphae in *Candida* cells.
Figure 4B:
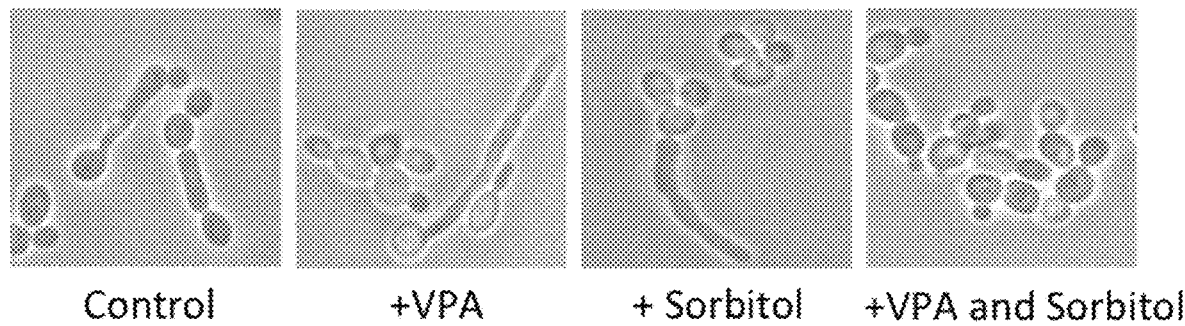

Valproate combined with Sorbitol greatly decreases the formation of hyphae in *Candida* cells. An overnight culture of *C. albicans* was prepared using serum-free RPMI-64 medium. Cells were pelleted at 7,500×g and resuspended in RPMI-64/10% FBS with or without 0.1M sorbitol and/or 2 mM VPA as indicated. Cultures were incubated at 37° C. in a rotary shaker at 200 rpm for 3 hours. For each sample, 300-500 cells were counted and the percentage of cells forming hyphal structures was calculated. Values represent the mean of three independent experiments±S.E. (error bars). See FIG. 4A. Phase contrast images of representative cells observed at magnification 1000× are shown in FIG. 4B.

Example 5

Figure 5:
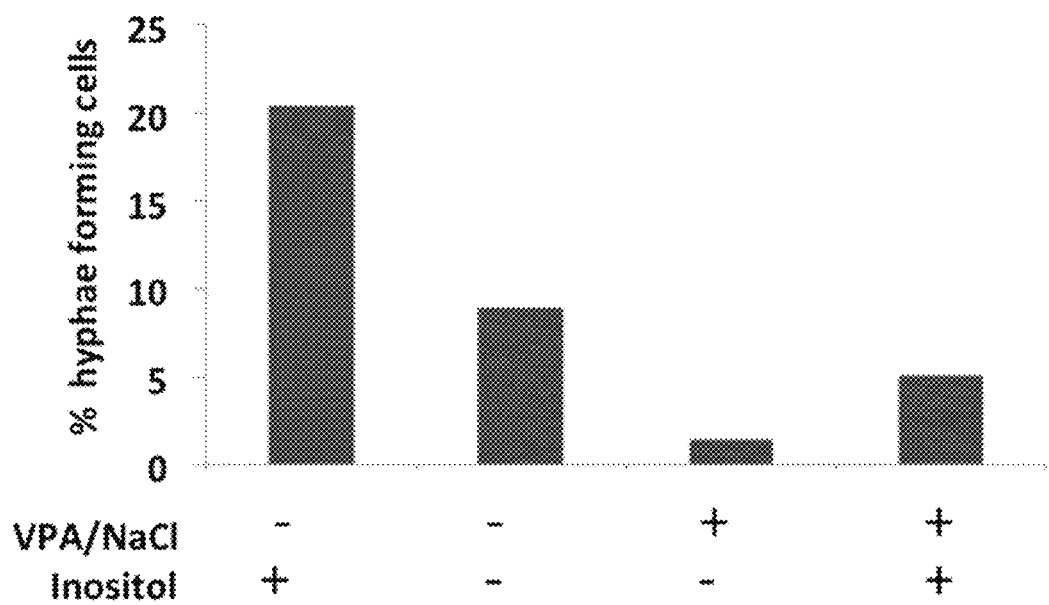
FIG. 5. The effect of VPA on hyphae formation is most likely due to inositol depletion.

The effect of VPA on hyphae formation is most likely due to inositol depletion. *C. albicans* cells were grown overnight in YPD medium. Cells were harvested, washed twice in distilled $H_2O$ to remove inositol, and resuspended in synthetic complete medium buffered to pH 7.0 in the presence or absence of VPA, NaCl and 75 µM inositol, as indicated. Cells were incubated at 37° C. in a rotary shaker at 200 rpm. Samples were collected after 3 hours of incubation, and the percentage of cells forming hyphae was determined. See FIG. 5.

Example 6

The following skin fungal burden assessment in a murine dermal infection model can be used to confirm the therapeutic effectiveness of various topical formulations:

Female Balb/c mice weighing 18-20 g, will be acclimated to housing conditions.

Mice will be fully immunocompetent and acclimated to the vivarium for a minimum of 24 hrs.

*C. albicans* (ATCC SC5314) will be grown for 24-48 hours at 35° C. at ambient atmosphere on Sabouraud dextrose agar plates. Scrapings of the fungal culture will be transferred to PBS and the concentration adjusted to $10^6$ CFU/mL with the aid of a spectrophotometer. Cultures will be diluted to provide inoculates of 6.0 logo CFU/mouse in 100 µl. The actual concentration of the stock suspensions will be verified using the dilution plate count method.

One day prior to infection the mice will be anaesthetized with isoflurane and an area of 1"×0.5" will be cleared of hair by shaving and the use of Nair. On the day of the infection, the mice will be anaesthetized with isoflurane. Immediately prior to infection, the test area of each mouse will receive 7 applications of tape stripping to remove the outermost layer of skin cells.

Mice will be infected using a topical application of 100 µl of the fungal inoculate, which is spread over a small infection site and allowed to dry slightly prior to bringing mice out of anesthesia.

Mice will be treated with test article, vehicle or positive control immediately following challenge via topical administration in a volume.

Mice will be treated once daily for 5 days (days 0-4).

On study Day 5, mice will be humanely euthanized via $CO_2$ overexposure. Skin will be aseptically excised from the infection area.

Excised skin will be transferred to vials containing 2.0 mL of sterile PBS, weighed and homogenized using a bead beater. The resulting homogenate will be serially diluted, and cultured on Sabouraud dextrose agar plates to enumerate colony forming units. Mean fungal burden per gram of skin tissue will be tabulated for each treatment condition.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in an embodiment's ability to provide a statistically significant beneficial effect in the skin fungal burden assessment model described in the prior paragraph.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A topical formulation comprising:
   2 mM valproate (VPA) or 2 mM valproic acid; and
   at least 0.1 M Sorbitol or more than 0.1 M sodium chloride.

2. The topical formulation of claim 1, further comprising a penetration enhancer.

3. The topical formulation of claim 2, wherein the penetration enhancer comprises a sulphoxide, an ether, a surfactant, an alcohol, a polyol, a fatty acid, an amide, a pyrrolidone, a terpene, or an azone.

4. The topical formulation of claim 1, wherein the VPA comprises sodium VPA.

5. The topical formulation of claim 1, comprising 2 mM VPA and at least 0.1 M Sorbitol.

6. The topical formulation of claim 1, comprising 2 mM valproic acid and at least 0.1 M Sorbitol.

7. A method of treating a fungal infection in a subject, comprising administering the topical formulation of claim 1 to the subject, thereby treating the fungal infection in the subject.

8. The method of claim 7, wherein the fungal infection comprises athlete's foot, penile thrush, ringworm, oncomycosis, thrush, vaginal yeast infection, or fungal eye infection.

9. The method of claim 7, wherein the fungal infection is caused by *Candida, Histoplasma, Microsporum, Epidermophyton, Trichophyton*, or a combination thereof.

10. A method of treating a fungal infection in a subject, comprising administering to the subject a formulation comprising 2 mM valproate (VPA) or 2 mM valproic acid and:
   at least 0.1 M Sorbitol; or
   more than 0.1 M sodium chloride.

11. The method of claim 10, wherein the formulation comprises a penetration enhancer.

12. The method of claim 11, wherein the penetration enhancer comprises at least one of a sulphoxide, an ether, a surfactant, an alcohol, a polyol, a fatty acid, an amide, a pyrrolidone, a terpene, or an azone.

13. The method of claim 10, wherein the VPA comprises sodium VPA.

14. The method of claim 10, wherein the formulation comprises 2 mM VPA and at least 0.1 M Sorbitol.

15. The method of claim 10, wherein the formulation comprises 2 mM valproic acid and at least 0.1 M Sorbitol.

16. The method of claim 10, wherein the fungal infection comprises systemic mycoses.

17. The method of claim 10, wherein the fungal infection is caused by *Aspergillus, Blastomyces, Candida, Cryptococcus, Histoplasma, Pneumocystis, Stachybotrys, Coccidioides, Microsporum, Epidermophyton, Trichophyton*, or a combination of two or more thereof.

* * * * *